United States Patent [19]

Nakagawa et al.

[11] Patent Number: 4,918,070
[45] Date of Patent: Apr. 17, 1990

[54] CEPHALOSPORIN DERIVATIVES AND ANTIBACTERIAL AGENTS

[75] Inventors: Susumu Nakagawa, Okazaki; Hiroshi Fukatsu, Nagoya; Yoshiaki Katoh, Okazaki; Satoshi Murase, Nagoya, all of Japan

[73] Assignee: Banyu Pharmaceutical Co., Ltd., Tokyo, Japan

[21] Appl. No.: 161,100

[22] Filed: Feb. 26, 1988

[30] Foreign Application Priority Data

Feb. 27, 1987 [JP] Japan .................................. 62-044166
Dec. 24, 1987 [JP] Japan .................................. 62-327695

[51] Int. Cl.$^4$ .................. C07D 501/26; A61K 31/545
[52] U.S. Cl. ...................................... 514/206; 514/203; 514/202; 540/222; 540/225; 540/227; 540/221
[58] Field of Search .............. 540/221, 222, 227, 225; 514/203, 206, 202

[56] References Cited

U.S. PATENT DOCUMENTS 4,405,778 9/1983 Scantazzini et al. ................ 540/222

FOREIGN PATENT DOCUMENTS 55687 5/1974 Japan .
108287 8/1975 Japan .
56489 5/1976 Japan .
63191 6/1976 Japan .
103493 9/1978 Japan .
76089 4/1984 Japan .
40292 2/1986 Japan .
130293 6/1986 Japan .
19594 11/1987 Japan .

Primary Examiner—Nicholas S. Rizzo
Attorney, Agent, or Firm—Oblon, Spivak, McClelland, Maier & Neustadt

[57] ABSTRACT

A cephalosporin derivative having the formula:

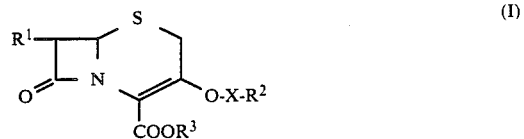

wherein $R^1$ is a substituted amino group, X is an alkylene group, $R^2$ is an aryl or heterocyclic group which may be substituted and $R^3$ is a hydrogen atom, a negative charge or a residue of an ester which can form a pharmaceutically acceptable ester hydrolyzable in a living body; or a pharmaceutically acceptable salt thereof.

4 Claims, No Drawings

CEPHALOSPORIN DERIVATIVES AND ANTIBACTERIAL AGENTS

The present invention relates to novel cephalosporin derivatives which are useful in the pharmaceutical fields, a process for their preparation and antibacterial agents.

The cephalosporin antibacterial agents have been widely used for the treatment of diseases caused by pathogenic bacteria in human and animals. For example, they are particularly useful for the treatment of infectious diseases caused by bacteria having resistance against Penicillin type antibacterial agents and for the treatment of infectious diseases of patients sensitive to Penicillin. Further, the cephalosporin antibacterial agents have low toxicity against animal cells, and thus they are superior also in the safety. Under the circumstances, many attempts have been made to provide cephalosporin antibacterial agents having stronger antibacterial activities and excellent safety.

Among such attempts, cephalosporin derivatives wherein the substituent at the 3-position of the cephalosporin nucleus is directly replaced by an oxygen atom are known and disclosed in Japanese Unexamined Patent Publications No. 55687/1974, No. 108287/1975, No. 56489/1976, No. 63191/1976, No. 103493/1978, No. 76089/1984, No. 40292/1986, No. 130293/1986 and No. 19594/1987. However, most of the compounds disclosed in these publications are used merely as intermediates, or the compounds simply have a lower alkoxy group such as a methoxy group as the substituent at the 3-position of the cephalosporin nucleus. Thus, the cephalosporin derivatives having at the 3-position of the cephalosporin nucleus an alkoxy group substituted by an aryl or heterocyclic group which may be substituted, have not been disclosed.

It is an object of the present invention to provide novel cephalosporin derivatives having not only excellent antibacterial activities but also excellent properties in the safety.

The present inventors have conducted an extensive research for novel cephalosporin derivatives having excellent antibacterial activities, and have found that a series of cephalosporin derivatives having at the 3-position of the cephalosporin nucleus an alkoxy group substituted by an aryl or heterocyclic group which may be substituted, show excellent antibacterial activities. The present invention has been accomplished based on the discovery. The present invention provides a compound having the formula:

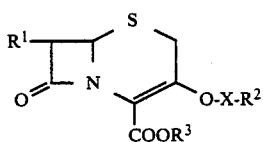

wherein $R^1$ is a substituted amino group, X is an alkenylene group, $R^2$ is an aryl or heterocyclic group which may be substituted and $R^3$ is a hydrogen atom, a negative charge or a residue of an ester which can form a pharmaceutically acceptable ester hydrolyzable in a living body; or a pharmaceutically acceptable salt thereof.

Further, the present invention provides a process for preparing the compound of the formula I, or a pharmaceutically acceptable salts thereof, which comprises reacting a compound having the formula:

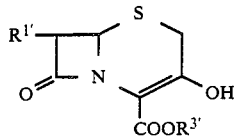

wherein $R^{1'}$ represents $R^1$ as defined above or $R^1$ with its functional group protected, $R^{3'}$ is a hydrogen atom, a carboxyl-protecting group or a residue of an ester which can form a pharmaceutically acceptable ester hydrolyzable in a living body, or a salt thereof, with a compound having the formula:

$$HO-X-R^{2'} \quad (III)$$

wherein X is an alkenylene group and $R^{2'}$ is an aryl or heterocyclic group which may be substituted, to form a compound having the formula:

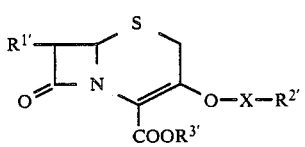

wherein $R^{1'}$, $R^{2'}$, $R^{3'}$ and X are as defined above, and optionally conducting one or more of the following steps:
(i) when $R^{2'}$ is a heterocyclic group, a step of introducing a substituent which may be protected to the heterocyclic group
(ii) a step of removing any protecting group
(iii) a step of converting the compound in the free form to a salt thereof, and
(iv) a step of forming a pharmaceutically acceptable ester hydrolyzable in a living body.

The present invention also provides an antibacterial agent comprising an antibacterially effective amount of the compound of the formula I or a pharmaceutically acceptable salt thereof, and a pharmaceutically acceptable carrier.

The definition of various terms referred to in this specification and some specific examples falling within such terms will be given.

The substituted amino group, means an amino group substituted by an acyl group, which is usually used as a substituent in cephalosporin and penicillin compounds. The acyl group includes an aliphatic acyl group, an acyl group having an aromatic ring (hereinafter referred to as an aromatic acyl group) and an acyl group having a heterocyclic ring (hereinafter referred to as a heterocyclic acyl group).

The aliphatic acyl group may be a lower or higher alkanoyl group having from 1 to 20 carbon atoms such as a formyl group, an acetyl group, a succinyl group, a hexanoyl group, a heptanoyl group or a stearoyl group, a lower alkoxycarbonyl group having from 2 to 8 carbon atoms such as a methoxycarbonyl group, an ethoxycarbonyl group, a tert-butoxycarbonyl group, a tert-pentyloxycarbonyl group or a heptyloxycarbonyl group, a lower alkanesulfonyl group having from 1 to 4 carbon atoms such as a methanesulfonyl group, an ethanesulfonyl group or a propanesulfonyl group, a lower alkenylthioalkanoyl group having from 4 to 8 carbon atoms such as a vinylthioacetyl group, an allylthioacety group, an allylthiopropionyl group or a butenylthioacetyl group, a lower alkylthioalkanoyl group having from 3 to 8 carbon atoms such as a methylthioacetyl group, an ethylthioacetyl group or a methylthiopropionyl group, or an unsaturated cycloalkenylalkanoyl group having from 8 to 10 carbon atoms such as a cyclohexenylacetyl group or cyclohexadienylacetyl group.

The aromatic acyl group may be an aroyl group having from 7 to 12 carbon atoms such as a benzoyl group, a toluoyl group or a naphthoyl group, an arylalkanoyl group having from 8 to 10 carbon atoms such as a phenylacetyl group or a phenylpropionyl group, an aryloxycarbonyl group having from 7 to 12 carbon atoms such as a phenoxycarbonyl group or a naphthyloxycarbonyl group, an arylalkoxycarbonyl group having from 8 to 10 carbon atoms such as a benzyloxycarbonyl group or a phenethyloxycarbonyl group, or an aryloxyalkanoyl group having from 8 to 10 carbon atoms such as a phenoxyacetyl group or a phenoxypropionyl group.

The heterocyclic acyl group may be a heterocyclic carbonyl group such as a thenoyl group, a furoyl group or a nicotinoyl group, a heterocyclic alkanoyl group such as a thienylacetyl group, a thiazolylacetyl group, a thiadiazolylacetyl group, a dithiinylacetyl group, a pyridylacetyl group, a pyrimidinylacetyl group, a triazolylacetyl group, a tetrazolyl acetyl group, a furylacetyl group, an oxazolylacetyl group or a thiadiazolylpropionyl group, or a heterocyclic oxy or thioalkanoyl group such as a pyridyloxyacetyl group, a pyridylthioacetyl group or a pyridyloxypropionyl group. The above-mentioned acyl group may have one or more substituents which may be the same or different. As the substituent, a halogen atom, an alkyl group which may be substituted, a hydroxyl group, a methoxy group, an ethoxy group, a fluoromethoxy group, a trifluoromethoxy group, a difluoromethoxy group, a formyloxy group, an acetoxy group, a fluoroacetoxy group, a carbamoyl group, an N-methylcarbamoyl group, an N,N-dimethylcarbamoyl group, a carbamoyloxy group, an N,N-dimethylcarbamoyloxy group, an N-methylcarbamoyloxy group, an amino group, an acetamide group, a formamide group, a fluoroacetamide group, a carboxyl group, a sulfo group, a sulfamoyl group, a cyano group, a =N-OR$^{13}$ group wherein R$^{13}$ is a hydrogen atom or a lower alkyl, cyclo alkyl, lower alkenyl, lower alkynyl, aryl, aralkyl or heterocyclic group which may be substituted, or a

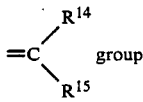 group wherein each of R$^{14}$ and R$^{15}$ which may be the same or different is a hydrogen atom, a halogen atom or a lower alkyl, aryl or aralkyl group which may be substituted.

The halogen atom includes a fluorine atom, a chlorine atom, a bromine atom and an iodine atom.

The lower alkyl group which may be substituted, may be an alkyl group having from 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a hexyl group or an isohexyl group, which may be substituted by one or more substituents such as a halogen atom, a hydroxyl group, a methoxy group, an ethoxy group, a propoxy group, a fluoromethoxy group, a difluoromethoxy group, a trifluoromethoxy group, a formyloxy group, an acetoxy group, a fluoroacetoxy group, an N-methylcarbamoyl group, a carbamoyl group, an N-methylcarbamoyloxy group, an N,N-dimethylcarbamoyl group, an N,N-dimethylcarbamoyloxy group, an amino group, a methylamino group, a dimethylamino group, a formamido group, an acetamido group, a fluoroacetamido group, a carboxyl group, a methoxycarbonyl group, an ethoxycarbonyl group, a sulfo group, a sulfamoyl group, a cyano group, a formyl group, an acetyl group, a fluoroacetyl group, a diethylamino group, an ethylamino group, a methylthio group, an ethylthio group, a propylthio group, a fluoromethylthio group, a 2-fluoroethylthio group, a 1-fluoroethylthio group, a tetrazolyl group, a 1-methyltetrazolyl group, a thiazolyl group, a 2-aminothiazolyl group, a 5-amino-1,2,4-thiadiazolyl group, a 1,2,4-thiadiazolyl group, a 1,2,3,-thiadiazolyl group, an imidazolyl group, a thienyl group, a furanyl group, a 2-aminoxazolyl group, an isothiazolyl group, an isoxazolyl group, a quinolyl group, an isoquinolyl group, a pyridyl group, a 3,4-dihydroxy-6-pyridyl group, a piperazinyl group, a piperidyl group, a pyrrolidinyl group, a pyrrolyl group, a morpholinyl group, a benzothiazolyl group or a benzimidazolyl group.

The cycloalkyl group which may be substituted, may be a cycloalkyl group having from 3 to 6 carbon atoms such as a cyclopropyl group, a cyclobutyl group, a cyclopentyl group or a cyclohexyl group, which may be substituted by one or more substituents such as a carbamoyl group, a carboxyl group, an amino group, a methylamino group, a dimethylamino group, a sulfo group, a hydroxyl group or a cyano group.

The alkenyl group which may be substituted, may be an alkenyl group having from 2 to 6 carbon atoms such as a vinyl group, an allyl group, a 1-propenyl group, a 2-propenyl group, an isopropenyl group, a 1-butenyl group, a 2-butenyl group, a 1-pentenyl group or a 1-hexenyl group, which may be substituted by one or more substituents such as a halogen atom, a carboxyl group, an amino group, a sulfo group, a hydroxyl group, a carbamoyl group or a cyano group.

The alkynyl group which may be substituted, may be an alkynyl group having from 2 to 6 carbon atoms such as an ethynyl group, a 1-propynyl group, a propargyl group, a 1-butynyl group, a 1-pentynyl group or a 1-hexynyl group which may be substituted by one or more substituents such as a halogen atom, a hydroxyl group, an amino group, a carboxyl group, a carbamoyl group, a sulfo group or a cyano group.

The aryl group which may be substituted, may be an aryl group having from 6 to 10 carbon atoms such as a phenyl or naphthyl group, which may be substituted by one or more substituents such as a halogen atom, a methyl group, a hydroxymethyl group, a fluoromethyl group, a trifluoromethyl group, an ethyl group, a bromomethyl group, a difluoromethyl group, a hydroxyl group, an aminomethyl group, a carboxymethyl group, a carbamoylmethyl group, a sulfomethyl group, an N-methylaminomethyl group, a methoxy group, an ethoxy group, a propoxy group, a fluoromethoxy group, an amino group, a methylamino group, a dimethylamino group, an ethylamino group, a propylamino group, a formamido group, an acetamido group, a propionylamino group, a formyloxy group, an acetoxy group, a propionyloxy group, a carboxyl group, a carbamoyl group, an N-methylcarbamoyl group, an N,N-dimethylcarbamoyl group, a methoxycarbamoyl group, an ethoxycarbamoyl group, a sulfamoyl group, a sulfo group, a cyano group or a nitro group.

The heterocyclic group which may be substituted, may be a monocyclic or dicyclic heterocyclic group containing from 1 to 4 hetero atoms selected from the group consisting of a nitrogen atom, a sulfur atom and an oxygen atom, such as a 1,2,3-thiadiazolyl group, a 1,3,4-thiadiazolyl group, a 1,2,4-thiadiazolyl group, a 1,2,3-triazolyl group, a 1,3,4-triazolyl group, a tetrazolyl group, a thiazolyl group, an isothiazolyl group, an oxazolyl group, an isoxazolyl group, an imidazolyl group, a pyridyl group, a pyrimidinyl group, a thienyl group, a furanyl group, a piperazinyl group, a piperidyl group, a morpholinyl group, a pyrrolidinyl group, a quinolyl group, an isoquinolyl group, a benzothiazolyl group or a benzimidazolyl group, which may be substituted by one or more substituents such as a halogen atom, a methyl group, an ethyl group, a propyl group, a hydroxymethyl group, an aminomethyl group, a sulfomethyl group, a carboxymethyl group, a cyanomethyl group, a fluoromethyl group, a chloromethyl group, a difluoromethyl group, a trifluoromethyl group, a carbamoylmethyl group, an N-methylcarbamoylmethyl group, a sulfamoylmethyl group, an oxo group, an N-methylaminomethyl group, an amino group, a methylamino group, a dimethylamino group, an ethylamino group, a methoxy group, an ethoxy group, a fluoromethoxy group, a difluoroethoxy group, a trifluoroethoxy group, a sulfamoyl group, a carboxyl group, a methoxycarbonyl group, a cyano group, a nitro group, a vinyl group, an allyl group, a propargyl group, an ethynyl group, an acetoxy group, a formyloxy group, a carbamoyloxy group, an N-methylcarbamoyloxy group, an acetamide group, a formamide group, an acetyl group, a fluoroacetyl group, a difluoroacetyl group, a trifluoroacetyl group, a hydroxyl group, a cyclopropyl group, a cyclobutyl group, a cyclopentyl group or a cyclohexyl group. When a positive charge arises due to the existence of a substituent in a nitrogen atom of the heterocyclic ring, an intramolecular salt or an intermolecular salt is formed.

The aralkyl group which may be substituted includes an aralkyl group having from 7 to 12 carbon atoms such as a benzyl group, a phenethyl group or a naphthylmethyl group, which may be substituted by one or more substituents such as a methyl group, an ethyl group, a propyl group, a halogen atom, a fluoromethyl group, a difluoromethyl group, a trifluoromethyl group, a carboxymethyl group, an aminomethyl group, a sulfomethyl group, a carbamoylmethyl group, an N-methylaminomethyl group, a methoxy group, an ethoxy group, a fluoroethoxy group, a difluoroethoxy group, a trifluoroethoxy group, a hydroxyl group, a formyloxy group, an acetoxy group, a trifluoroacetoxy group, an amino group, a methylamino group, an ethylamino group, a dimethylamino group, a diethylamino group, a formamido group, an acetamido group, a carboxyl group, a methoxycarbonyl group, an ethoxycarbonyl group, a carbamoyl group, an N-methylcarbamoyl group, an N,N-dimethylcarbamoyl group, a sulfo group, a cyano group or a nitro group.

The alkenylene group may be a straight chain, branched chain or cyclic alkenylene group having from 1 to 6 carbon atoms such as a methylene group, an ethylene group, an ethylidene group, an isopropylidene group, a propylene group, a trimethylene group, a tetramethylene group, a 1,2-cyclopentylene group, a 1,3-cyclopentylene group, a 1,2-cyclohexylene group, a 1,3-cyclohexylene group or a 1,4-cyclohexylene group.

The carboxyl-protecting group may be a carboxyl-protecting group which can be easily removed by an acid hydrolysis, a catalytic reduction, etc., such as a tert-butyl group, a phenyl group, a methoxymethyl group, an ethoxymethyl group, a benzyl group, a p-methoxybenzyl group, a p-nitrobenzyl group or a benzhydryl group.

The amino-protecting group may be an amino-protecting group which can be easily removed by an acid hydrolysis, a catalytic reduction, etc., such as a trityl group, a formyl group, a chloroacetyl group, a trifluoroacetyl group, a tert-butoxycarbonyl group, a trimethylsilyl group or a tert-butyldimethylsilyl group.

The residue of an ester which can form a pharmaceutically acceptable ester hydrolyzable in a living body, may be a lower alkanoyloxymethyl group such as an acetoxymethyl group, a propionyloxymethyl group or a pivaloyloxymethyl group; a 1-(lower alkoxycarbonyloxy)ethyl group such as a 1-(methoxycarbonyloxy)ethyl group, a 1-(ethoxycarbonyloxy)ethyl group or a 1-(tert-butoxycarbonyloxy)ethyl group; a 5-substituted-2-oxo-1,3-dioxol-4-ylmethyl group such as 5-methyl-2-oxo-1,3-dioxol-4-ylmethyl group or a 5-phenyl-2-oxo-1,3-dioxol-4-ylmethyl group; a 1-phthalidyl group or a 5-cyano-1-phthalidyl group.

In the compound of the formula I of the present invention, $R^1$ is preferably an amino group which is substituted by an acyl group, such as a (2-fluoro-2-carbamoylvinylthio)acetyl group, a 2-difluoromethylthioacetyl group, a 2-phenylacetyl group, a 2-amino-2-phenylacetyl group, a 2-amino-2-(4-hydroxyphenyl)acetyl group, a 2-carboxy-2-phenylacetyl group, a 2-carboxy-2-(4-hydroxyphenyl)acetyl group, a 2-(4-hydroxyphenyl)-2-[(4-ethyl-2,3-dioxo-1-piperazinyl)carbonylamino]acetyl group, a 2-phenyl-2-[(4-ethyl-2,3-dioxo-1-piperazinyl)carbonylamino]acetyl group, a 2-sulfo-2-phenylacetyl group, a 2-hydroxy-2-phenylacetyl group, a 2-(1,4-cyclohexadienyl)acetyl group, a 2-amino-2-(1,4-cyclohexadienyl)acetyl group, a 2-(2-thienyl)acetyl group, a 2-(2-furanyl)acetyl group, a 2-(2-aminomethylphenyl)acetyl group, a 2-carboxy-2-(3-thienyl)acetyl group, a 2-tetrazolylacetyl group, a 2-methoxyimino-2-(2-thienyl)acetyl group, a 2-methoxyimino-2-(2-furanyl)acetyl group, a 2-(4-pyridylthio)acetyl group, a 2-(4-pyridyloxy)acetyl group, a 2-hydroxyimino-2-phenylacetyl group, a 2-cyanomethylthioacetyl group, a 2-(2-fluorovinylthio)acetyl group, a 2-trifluoromethylthioacetyl group, a 2-(2-aminothiazol-4-yl)acetyl group, a 2-methoxyimino-2-(2-aminothiazol-4-yl)acetyl group, a 2-ethoxyimino-2-(2-aminothiazol-4-yl)acetyl group, a 2-propoxyimino-2-(2-aminothiazol-4-yl)acetyl group, a 2-isopropoxyimino-2-(2-aminothiazol-4-yl)acetyl group, a 2-butoxyimino-2-(2-aminothiazol-4-yl)acetyl group, a 2-sec-butoxyimino-2-(2-aminothiazol-4-yl)acetyl group, a 2-tert-butoxyimino-2-(2-aminothiazol-4-yl)acetyl group, a 2-pentyloxyimino-2-(2-aminothiazol-4-yl)acetyl group, a 2-hexyloxyimino-2-(2-aminothiazol-4-yl)acetyl group, a 2-hydroxyimino-2-(2-aminothiazol-4-yl)acetyl group, a 2-cyclopropoxyimino-2-(2-aminothiazol-4-yl)acetyl group, a 2-cyclobutoxyimino-2-(2-aminothiazol-4-yl)acetyl group, a 2-cyclopentyloxyimino-2-(2-aminothiazol-4-yl)acetyl group, a 2-cyclohexyloxyimino-2-(2- aminothiazol-4-yl) -acetyl group, a 2-(1-carboxy-1-cyclopropoxyimino)-2-(2-aminothiazol-4-yl)acetyl group, a 2-(1-carboxy-1-cylcobutoxyimino)-2-(2-aminothiazol-4-yl)acetyl group, a 2-(1-carboxy-1-cyclopentyloxyimino)-2-(2-aminothiazol-4-yl)acetyl group, a 2-(1-carboxy-1-cyclohexyloxyimino)-2-(2-aminothiazol-4-yl)acetyl group, a 2-carboxymethoxyimino-2-(2-aminothiazol-4-yl)acetyl group, a 2-(2-carboxyethoxyimino)-2-(2-aminothiazol-4-yl)acetyl group, a 2-(1-carboxyethoxyimino)-2-(2-aminothiazol-4-yl)acetyl group, a 2-(1-carboxy-1-methylethoxyimino)-2-(2-aminothiazol-4-yl)acetyl group, a 2-(1carboxy-1-ethenyloxyimino)-2-(2-aminothiazol-4-yl)acetyl group, a 2-(2-carboxymethyl-1-ethenyloxyimino)-2-(2-aminothiazol-4-yl)acetyl group, a 2-fluoromethoxyimino-2-(2-aminothiazol-4-yl)acetyl group, a 2-(2-chloroethoxyimino-2-(2-aminothiazol-4-yl) acetyl group, a 2-bromomethoxyimino-2-( 2-aminothiazol-4-yl) acetyl group, a 2-( 2-fluoroethoxyimino)-2-(2-aminothizol-4-yl) acetyl group, a 2-(2-chloroetho xyimino)-2-(2-aminothiazol-4-yl) acetyl group, a 2-(1-fluoro-1-methylethoxyimino)-2-(2-aminothiazol-4-yl)acetyl group, a 2-benzyloxyimino-2-(2-aminothiazol-4-yl)acetyl group, a 2-(3,4-dihydroxybenzyloxyimino)-2-(2-aminothiazol4-yl)acetyl group, a 2-(α-carboxy-3,4-dihydroxybenzyloxyimino)-2-(2-aminothiazol-4-yl)acetyl group, a 2-(α-carboxybenzyloxyimino)-2-(2-aminothiazol-4-yl)acetyl group, a 2-(2-carboxymethylbenzyloxyimino) -2-(2-aminothiazol-4-yl)acetyl group, a 2-(2-carboxybenzyloxyimino)-2-(2-aminothiazol-4-yl)acetyl group, a 2-methoxyimino-2-(5-amino-1,2,4-thiadiazol-3-yl)acetyl group, a 2-(2-fluoroethoxyimino)-2-(5-amino-1,2,4-thiadiazol-3-yl)acetyl group, a 2-(1-carboxy-1-ethenyloxyimino)-2-(5-amino-1,2,4-thiadiazol-3-yl)acetyl group, a 2-(1-carboxy-1-methylethoxyimino)-2-(5-amino -1,2,4-thiadiazol-3-yl)acetyl group, a 2-(α-carboxy-3,4-dihydroxybenzyloxyimino)-2-(5-amino-1,2,4-thiadiazol-3-yl)acetyl group, a 1-(2-aminothiazol-4-yl)-1-propenylcarbonyl group, a 2-benzylidene-2-(2-aminothiazol-4-yl)acetyl group, a 2-chloromethylene-2 (2-aminothiazol-4-yl)acetyl or a 2-fluoromethylene-2-(2-aminothiazol-4-yl)acetyl group.

The —O—X—R² group of the present invention is preferably a benzyloxy group, a 4-cyanobenzyloxy group, a 4-nitrobenzyloxy group, a 4-carboxybenzyloxy group, a 4-carbamoylbenzyloxy group, a 3,4-dihydroxybenzyloxy group, a thiazol-4ylmethoxy group, a thiazol-2-ylmethoxy group, a thiazol-5-ylmethoxy group, a 4-methylthiazol-2-ylmethoxy group, a 2-methylthiazol-5-ylmethoxy group, a 1,2,3-thiadiazol-4-ylmethoxy gruop, a 1,2,4-thiadiazol-3-ylmethoxy group, a 1,3,4-thiadiazol-2-ylmethoxy group, a 1-methylimidazol-2-ylmethoxy group, a 2-pyrrolidon-5-ylmethoxy group, a 1-methyl-2-pyrrolidon-5-ylmethoxy group, a tetrazol-5-ylmethoxy group, a 1,3,4-triazol-2-ylmethoxy group, a 2-pyridylmethoxy group, a 3-pyridylmethoxy group, a 4-pyridylmethoxy group, a 1-methyl-2-pyridiniomethoxy group, a 1-methyl-3-pyridiniomethoxy group, a 1-methyl-4-pyridiniomethoxy group, a 1-ethyl-2-pyridiniomethoxy group, a 1-ethyl-4-pyridiniomethoxy group, a 1-propyl-4-pyridiniomethoxy group, a 1-allyl-2-pyridiniomethoxy group, a 1-allyl-4-pyridiniomethoxy group, a 1-carboxymethyl-3-pyridiniomethoxy group, a 1-carboxymethyl-4-pyridiniomethoxy group, a 1-carbamoylmethyl-2-pyridiniomethoxy group, a 1-carbamoylmethyl-4-pyridiniomethoxy group, a 1-(2-pyridyl)ethoxy group, a 1-(3-pyridyl)ethoxy group, a 1-(4-pyridyl)ethoxy group, a 1-(1-methyl-4-pyridinio)ethoxy group, a 1-(1-methyl-3-pyridinio)ethoxy group, a 1-(1-methyl-2-pyridinio)ethoxy group, a 2-(2-pyridyl)ethoxy group, a 2-(3-pyridyl)ethoxy group, a 2-(4-pyridyl)ethoxy group, a 2-(1-methyl-2-pyridinio)ethoxy group, a 2-(1-methyl-3-pyridinio)ethoxy group, a 2-(1-methyl-4-pyridinio)ethoxy group, a 3,4-dihydroxy-1-methyl-6-pyridiniomethoxy group, a 3,4-dihydroxy-1-(2-fluoroethyl)-6-pyridiniomethoxy group, a 2-chloro-1-methyl-4-pyridiniomethoxy group, a 1,2-dimethyl-4-pyridiniomethoxy group, a 2-carbamoyl-1-methyl-4-pyridiniomethoxy group, a 3-carboxy-1-methyl-5-pyridiniomethoxy group, a 4-hydroxy-1-methyl-2-pyridiniomethoxy group, or a 1-(2-methoxy-4-pyridyl)ethoxy group.

The pharmaceutically acceptable salt of the compound of the formula I may be a salt with an alkali metal such as sodium, potassium or lithium, a salt with an alkaline earth metal such as calcium or magnesium, a salt with an organic amine such as N,N-dibenzylethylenediamine, ethanolamine or triethylamine, a salt with an inorganic acid such as hydrochloric acid, nitric acid sulfuric acid or phosphoric acid, a salt with an organic acid such as acetic acid, citric acid or tartaric acid, a salt with an organic sulfonic acid such as methanesulfonic acid or p-toluenesulfonic acid or a salt with an amino acid such as aspartic acid, glutamic acid or lysine.

Now, the process for the preparation of the compounds of the present invention will be described.

The compound of the formula I of the present invention can be prepared by reacting a compound having the formula:

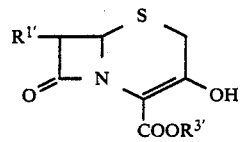

(II)

wherein $R^{1'}$ represents $R^1$ as defined above or $R^1$ with its functional group protected, $R^{3'}$ is a hydrogen atom, a carboxyl-protecting group or a residue of an ester which can form a pharmaceutically acceptable ester hydrolyzable in a living body, or a salt thereof, with a compound having the formula:

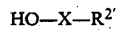

(III)

wherein X is an alkenylene group and $R^{2'}$ is an aryl or heterocyclic group which may be substituted, to form a compound having the formula:

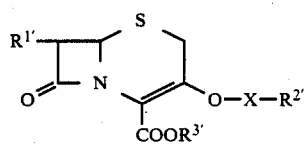

(IV)

wherein $R^{1'}$, $R^{2'}$, $R^{3'}$ and X are as defined above, and optionally conducting one or more of the following steps:

(i) when $R^{2'}$ is a heterocyclic group, a step of introducing a substituent which may be protected to the heterocyclic group (ii) a step of removing any protecting group (iii) a step of converting the compound in the free form to a salt thereof, and (iv) a step of forming a pharmaceutically acceptable ester hydrolyzable in a living body.

The reaction of the compound of the formula II with the compound of the formula III to produce the compound of the formula IV, may be conducted in an organic solvent which does not adversely affect the reaction, for example, in an aromatic hydrocarbon such as benzene or toluene, in an ether such as diethyl ether, tetrahydrofuran or dioxane, in a chlorinated hydrocarbon such as methylene chloride or chloroform, or an acid amide such as N,N-dimethylformamide or N,N-dimethylacetamide, in the presence of an azodicarboxylate reagent, and a trialkylphosphine or a triarylphosphine.

The azodicarboxylate reagent used in this reaction may be dimethylazodicarboxylate, diethylazodicarboxylate or diisopropylazodicarboxylate, and is preferably diethylazodicarboxylate. The trialkylphosphine or the triarylphosphine may be triethylphosphine, tributylphosphine or triphenylphosphine, and is preferably triphenylphosphine.

As the reaction conditions of this step, an amount of each starting materials and reagents may suitably be selected. Preferably, the molar ratio of the compound of the formula II, the compound of the formula III, the azodicarboxylate reagent and the phosphine is about 1:1:1:1. The reaction temperature may suitably be selected from the range of from $-50°$ C. to the reflux temperature. The reaction temperature is preferably from $-30°$ C. to room temperature, and the reaction time may be from 5 minutes to 24 hours.

When R' of the compound of the formula IV thus obtained is a heterocyclic group, the step of introducing a substituent to the heterocyclic group, may be conducted by reacting the compound of the formula IV with an alkylating agent in a non-aqueous solvent such as methylene chloride, chloroform, tetrahydrofuran, acetone, acetonitrile, N,N-dimethylformamide or N,N-dimethylacetamide, or in a mixture of such solvents.

The alkylating agent used in this step, may be a lower alkyl iodide such as methyl iodide, ethyl iodide, propyl iodide, isopropyl iodide or butyl iodide, an alkenyl iodide such as an allyl iodide 1-butenyl iodide, dimethyl sulfate, an alkyl sulfonate which may be substituted by a halogen atom such as methylfluoro sulfonate, methyltrifluoromethane sulfonate or ethyltrifluoromethane sulfonate, a benzhydryl iodoacetate or iodoacetamide.

The reaction of this step usually conducted at a temperature from $-10°$ to $50°$ C., preferably at room temperature, for 1 to 48 hours, preferably for 24 hours.

If the products prepared by the above-mentioned steps have a protecting group, the protecting group is removed by a method suitably selected, depending upon the type of the protecting group, from conventional method disclosed in, for example, Protective Groups in Organic Synthesis published in 1981. For instance, the amino-protecting group is removed as follows: a tert-butoxycarbonyl group or a trityl group is removed by an acid, a 2,2,2-trichloroethoxycarbonyl group is removed by zinc and an acid, and a p-nitrobenzyloxycarbonyl group is removed by a catalytic reduction. For instance, the hydroxyl-protecting group is removed as follows: a formyl group or a trifluoroacetyl group is removed by potassium hydrogen carbonate in hydrous methanol, a tetrahydropyranyl group is removed by dilute hydrochloric acid, and a 2,2,2-trichloroethoxycarbonyl group is removed by zinc and an acid. For instance, the carboxyl-protecting group is removed as follows: a benzhydryl group or a p-methoxybenzyl group is removed by an acid such as trifluoroacetic acid in the presence of anisole, a 2-methylsulfonyl group is removed by an alkali, a trimethylsilyl group or a tert-butyldimethylsily group is removed by water or a hydrous alcohol, a 2,2,2-trichloroethyl group is removed by zinc and an acid, and a p-nitrobenzyl group is removed by reduction. The product obtained from each step can be purified by column chromatography, extraction with a solvent, precipitation, recrystallization, etc. Further, the product can be converted to a desired salt or ester by a conventional method, if necessary.

The starting material of the formula II of the present invention can be prepared by reacting 7-amino-3-hydroxy-3-cephem-4-carboxylic acid prepared by a method described in Helvetica Chimica Acta, vol. 57, page 1919 (1974) with a desired active derivative such as a mixed acid anhydride, an acid halide, an azide or an active ester. As the compound of the formula III, a compound commercially available or a compound readily prepared by a conventional method can be used.

The compound of the present invention shows excellent antibacterial activities, and is useful for a medicine. It can be used for the treatment or prevention of infectious diseases caused by bacteria, such as respiratory infectiousness, infectiousness of the genito-urinary tract, suppurative diseases and surgical infectiousness.

As the administration method, non-oral administration such as injection into veins, injection into muscles or suppositories, or oral administration such as tablets, powders, capsules, or syrups may be mentioned. Such formulations are prepared by a usual method in this field, and may contain additives which are commonly used, such as assisting agents, stabilizers, wetting agents and emulsifying agents. The dose may vary depending upon the age, sex, weight, sensitivity, administration method, administration period or interval, condition of the patient, properties, method or type of formulations and type of the active ingredient, and should be determined by a doctor. The daily dose is usually within a range of from 1 to 100 mg/kg, which is preferably administered in 2 to 4 times per day, each time with a dose of from 5 to 30 mg/kg.

To demonstrate the usefulness of the compounds of the present invention, the in vitro antibacterial activities of the compounds of the present invention against various microorganisms were measured by the following agar plate dilution method. One platinum loopfull of each test microorganism incubated overnight in Mueller Hinton broth, was inoculated to Mueller Hinton agar (inoculum size: $10^6$ CFU/ml). Such culture media containing various antibiotics in various concentrations were prepared. After incubation at $37°$ C. for 16 hours, the minimum inhibitory concentrations (MIC: $\mu$g/ml) were measured. The results are shown in the following Table 1.

TABLE 1

| Minimum Inhibitory Concentration ($\mu$g/ml, $10^6$ CFU/ml, MH agar) | | | | | | |
|---|---|---|---|---|---|---|
| Compound | Compound | Compound | Compound | Compound | Compound | Compound |

TABLE 1-continued

| Test microorganism | of Ex. 1 | of Ex. 4 | of Ex. 12 | of Ex. 14 | of Ex. 16 | of Ex. 18 | of Ex. 22 |
|---|---|---|---|---|---|---|---|
| S. aureus 209P NIHJ-JCl | 0.780 | 12.5 | 0.780 | 3.12 | 3.12 | 3.12 | 50.0 |
| E. coli NIHJ JC2 | 0.200 | 0.390 | 0.780 | 0.390 | 0.200 | 0.390 | 0.050 |
| K. pneumoniae PCI-602 | <0.006 | 0.050 | 0.0125 | <0.006 | <0.006 | 0.0125 | 0.025 |
| P. vulgaris HX-19 | 0.050 | 0.0125 | 0.025 | 0.050 | <0.006 | 0.100 | 0.025 |
| S. marcescens IAM 1184 | 0.100 | 0.025 | 0.390 | 0.100 | 0.200 | 0.390 | 0.0125 |
| E. cloacae 963 | 0.200 | 0.039 | 0.780 | 0.200 | 0.200 | 0.390 | 0.100 |

| | Minimum Inhibitory Concentration ($\mu$g/ml, $10^6$ CFU/ml, MH agar) | | | | | | |
|---|---|---|---|---|---|---|---|
| Test microorganism | Compound of Ex. 32 | Compound of Ex. 36 | Compound of Ex. 37 | Compound of Ex. 38 | Compound of Ex. 40 | Compound of Ex. 44 | Compound of Ex. 51 |
| S. aureus 109P NIHJ-JCl | 0.039 | 6.25 | 1.56 | 0.039 | 1.56 | 0.200 | 3.12 |
| E. coli NIHJ JC2 | 0.100 | 0.050 | 0.025 | 0.039 | 0.390 | 0.390 | 0.200 |
| K. pneumoniae PCI-602 | 0.025 | 0.0125 | <0.006 | 0.025 | 0.050 | 0.050 | 0.025 |
| P. vulgaris HX-19 | 0.200 | 0.050 | 0.025 | 0.390 | 0.0125 | 0.200 | 0.050 |
| S. marcescens IAM 1184 | 0.050 | 0.025 | <0.006 | 0.100 | 0.100 | 0.200 | 0.100 |
| E. cloacae 963 | 0.100 | 0.050 | 0.025 | 0.039 | 0.390 | 0.200 | 0.100 |

Now, the present invention will be described with reference to Examples. However, it should be understood that the present invention is by no means restricted by these specific Examples.

EXAMPLE 1

Sodium 7$\beta$-[2-(2-aminothiazol-4-yl)-(Z)-2-methoxyiminoacetamido]-3-(4-pyridylmethoxy)-3-cephem-4-carboxylate 2.29 g (3.01 mmol) of p-methoxybenzyl 7$\beta$-[2-(2-tritylaminothiazol-4-yl)-(Z)-2-methoxyiminoacetamido]-3-hydroxy -3-cephem-4-carboxylate and 982 mg (3.75 mmol) of triphenylphosphine were dissolved in 48 ml of tetrahydrofuran, and a solution of 408 mg (3.74 mmol) of 4-pyridinemethanol in 24 ml of tetrahydrofuran was added thereto at room temperature under nitrogen atmosphere. Then, a solution of 0.58 ml (3.67 mmol) of diethylazodicarboxylate in 24 ml of tetrahydrofuran was dropwise added thereto at room temperature, and the mixture was stirred for 2 hours at the same temperature. The solvent was distilled off. The residue was dissolved in ethyl acetate, washed sequentially with water, a saturated sodium hydrogencarbonate aqueous solution and a saturated sodium chloride aqueous solution and dried over magnesium sulfate. The solvent was distilled off and the residue was purified by silica gel column chromatography (Wakogel C-300, elution with 1% methanol-chloroform) to obtain 1.46 g (yield: 56.9%) of p-methoxybenzyl 7$\beta$-[2-(2-tritylaminothiazol-4-yl)-(Z) -2-methoxyiminoacetamido]-3-(4-pyridylmethoxy) -3-cephem-4-carboxylate as a light yellow powder. 660 mg (0.774 mmol) of this powder was dissolved in 4.1 ml of dichloromethane and 0.9 ml of anisole, and 6.6 ml of trifluoroacetic acid was dropwise added thereto under cooling with ice. The mixture was stirred for 1 hour at the same temperature. The solvent was distilled off, and isopropyl ether was added to the residue to obtain the trifluoroacetate of the above-identified compound as a powder. This trifluoroacetate was dissolved in water and adjusted to pH6.5 with a sodium hydrogencarbonate aqueous solution. The solution was purified by reversed phase column chromatography (Chemco LC-SORB, SP-B-ODS, elution with 20% methanol aqueous solution) and freeze-dried to obtain 221 mg (yield: 55.7%) of the above-identified compound.

MP: 175° C. (decomposed)
IR(KBr)cm$^{-1}$: 1760, 1670, 1620, 1540
NMR(DMSO-d$_6$)$\delta$: 3.45(2H, br), 3.86(3H, s), 5.02(1H, d, J=4.5 Hz), 5.03(2H, s), 5.5(1H, dd, J=4.5 Hz & 8 Hz), 6.75(1H, s), 7.22(2H, br), 7.41(2H, d, J=5 Hz), 8.5(2H, d, J=5 Hz), 9.47(1H, d, J=8 Hz)

The following compounds of Examples 2-29 were synthesized in the same manner as in Example 1.

EXAMPLE 2

Sodium 7$\beta$-[2-(2-aminothiazol-4-yl)-(Z)-2-ethoxyiminoacetamido]-3-(4-pyridylmethoxy)-3-cephem-4-carboxylate MP: 170° C. (decomposed)
IR(KBr)cm$^{-1}$: 1760, 1640, 1620, 1635 NMR(DMSO-d$_6$)$\delta$: 1.2(3H, t, J=7 Hz), 4.08(2H, q, J=7 Hz), 5.01(3H, bs) 5.50(1H, dd, J=5 & 7 Hz), 6.7(1H, s), 7.19(2H, br), 7.39(2H, d, J=5 Hz), 8.48(2H, d, J=5 Hz), 9.43(1H, d, J=7 Hz)

EXAMPLE 3

Disodium 7$\beta$-[2-(2-aminothiazol-4-yl)-(Z)-2-carboxylatomethoxyiminoacetamido]-3-(4-pyridylmethoxy)-3-cephem-4-carboxylate MP170° C. (decomposed)
IR(KBr)cm$^{-1}$: 1760, 1610, 1535
NMR(DMSO-d$_6$)$\delta$: 4.3(2H, bs), 9.95–5.1(3H, m), 5.51(1H, dd, J=4.5 & 8 Hz), 6.81(1H, s), 7.2(2H, br), 7.39(2H, d, J=5 Hz), 8.49(2H, d, J=5 Hz), 11.71(1H, d, J=8 Hz)

EXAMPLE 4

Disodium 7$\beta$-[2-(2-aminothiaxol-4-yl)-(Z)-2-(1-carboxylato-1-methylethoxyimino)acetamido]-3-(4-pyridylmethoxy)-3-cephem-4-carboxylate MP: 180° C. (decomposed)
IR(KBr)cm$^{-1}$: 1760, 1560–1680, 1530
NMR(DMSO-d$_6$)$\delta$: 1.38(3H, s), 1.45(3H, s), 5.0(3H, bs), 5.55(1H, dd, J=4.5 & 8 Hz), 6.69(1H, s), 7.17(2H, bs), 7.38(2H, d, J=5 Hz), 8.48(2H, d, J=5 Hz), 1.44(1H, d, J=8 Hz)

EXAMPLE 5

Disodium 7$\beta$-[2-(2-aminothiazol-4-yl)-(z)-2-(1-carboxylatovinyloxyimino)acetamido]-3-(4-pyridylmethoxy)-3-cephem-4-carboxylate MP: 175° C. (decomposed)
IR(KBr)cm$^{-1}$: 1760, 1600, 1535

NMR(DMSO-d₆)δ: 4.86(1H, bs), 5.01(3H, bs), 5.16(1H, bs), 5.53(1H, m), 6.90(1H, s), 7.26(2H, bs), 7.4(2H, d, J=5 Hz), 8.49(2H, d, J=5 Hz)

EXAMPLE 6

Sodium 7β-[2-(5-amino-1,2,4-thiadiazol-3-yl)-(Z)-2-ethoxyiminoacetamido]-3-(4-pyridylmethoxy)-3-cephem-4-carboxylate MP: 190° C. (decomposed)
IR(KBr)cm⁻¹: 1760, 1600, 1530, 1410
NMR(DMSO-d₆)δ: 1.25(3H, t, J=8 Hz), 3.4(2H, bs), 4.16(2H, m), 5.0(3H, bs), 5.55(2H, dd, J=5 & 8 Hz), 7.42(2H, d, J=5 Hz), 8.2(2H, bs), 8.5(2H, d, J=5 Hz), 9.42(1H, d, J=8 Hz)

EXAMPLE 7

7β-(D-2-amino-2-phenylacetamido)-3-(4-pyridylmethoxy)-3-cephem-4-carboxylic acid MP: 165° C. (decomposed)
IR(KBr)cm⁻¹: 3430, 3050, 1755, 1670, 1600, 1410
NMR(DMSO-d₆)δ: 3.45(2H, bs), 4.52(2H, bs), 4.9(1H, d, J=5 Hz), 4.99(1H, bs), 5,44(1H, d, J=5 Hz), 7.44(7H, m), 8.5(2H, d, J=4 Hz), 8.76(1H, br)

EXAMPLE 8

Sodium 7β-[2-(2-aminothiazol-4-yl)-(Z)-2-methoxyiminoacetamido]-3-(3-pyridylmethoxy)-3-cephem-4-carboxylate MP: 175° C. (decomposed)
IR(KBr)cm⁻¹: 1760, 1580–1680, 1540
NMR(DMSO-d₆+D₂O)δ: 3.39(2H, bs), 3.86(3H, s), 5.0(3H, bs), 5.49(1H, d, J=4 Hz), 6.77(1H, s), 7.37(1H, dd, J=4.5 & 8 Hz), 7.9(1H, d, J=8 Hz), 8.48(1H, d, J=4.5 Hz), 8.58(1H, s)

EXAMPLE 9

Sodium 7β-[2-(2-aminothiazol-4-yl)-(Z)-2-methoxyiminoacetamido]-3-(2-pyridylmethoxy)-3-cephem-4-carboxylate MP: 140° C. (decomposed)
IR(KBr)cm⁻¹: 1760, 1600–1680, 1530
NMR(DMSO-D₆+D₂O)δ: 3.08, 3.4(2H, ABq, J=13 Hz), 3.88(3H, s), 5.05–5.25(1H, m), 5.4–5.75(3H, m), 6.77(1H, s), 7.8–8.25(2H, m), 8.57(1H, d, J=6.5 Hz), 8.99(1H, d, J=6 Hz)

EXAMPLE 10

Sodium 7β-[2-(2-aminothiazol-4-yl)-(Z)-2-methoxyiminoacetamido]-3-[2-(2-pyridyl)ethoxy]-3-cephem-4-carboxylate MP: 180° C. (decomposed)
IR(KBr)cm⁻¹: 1760, 1580–1680, 1540
NMR(DMSO-D₆+D₂O)δ: 3.04(2H, t, J=6.5 Hz), 3.21(2H, bs), 3.86(3H, s), 4.2(2H, t, J=6.5 Hz), 4.97(1H, d, J=5 Hz), 5.46(1H, d, J=5 Hz), 6.77(1H, s), 7.0–7.5(2H, m), 7.67(1H, d, J=8 Hz), 8.45(1H, d, J=5 Hz)

EXAMPLE 11

Sodium 7β-[2-(2-aminothiazol-4-yl)-(Z)-2-methoxyiminoacetamido]-3-[1-(4-pyridyl)ethoxy]-3-cephem-4carboxylate MP: 175°–180° C. (decomposed)
IR(KBr)cm⁻¹: 1760, 1660, 1600, 1530

EXAMPLE 12

Sodium 7β-[2-(2-aminothiazol-4-yl)-(Z)-2-methoxyiminoacetamido]-3-(4-cyanobenzyloxy)-3-cephem-4-carboxylate MP: 175°–180° C. (decomposed)
IR(KBr)cm⁻¹: 2230, 1760, 1610, 1530, 1360
NMR(DMSO-d₆)δ: 3.4(m), 3.88(3H, s), 4.95–5.1(3H, m), 5.4(1H, dd, J=5 & 8 Hz), 6.75(1H, s), 7.27(2H, br), 7.62(2H, d, J=8 Hz), 7.79(2H, d, J=8 Hz), 9.5(1H, d, J=8 Hz)

EXAMPLE 13

Sodium 7β-[2-(2-aminothiazol-4-yl)-(Z)-2-methoxyiminoacetamido]-3-(4-nitrobenzyloxy)-3-cephem-4-carboxylate MP: 165°–170° C. (decomposed)
IR(KBr)cm⁻¹: 1760, 1600, 1520, 1360
NMR(DMSO-d₆)δ: 3.4(m), 3.86(3H, s), 5.02(1H, d, J=5 Hz), 5.12(2H, s), 5.55(1H, m), 6.75(1H, s), 7.25(2H, br), 7.72(2H, d, J=9 Hz), 8.2(2H, d, J=9 Hz), 9.5(1H, bd, J=8 Hz)

EXAMPLE 14

Sodium 7β-[2-(2-aminothiazol-4-yl)-(Z)-2-methoxyiminoacetamido]-3-(4-carbamoylbenzVloxy)-3-cephem-4-carboxylate MP : 190°–195° C. (decomposed)
IR(KBr)cm⁻¹: 1755, 1660, 1615, 1530
NMR(DMSO-d₆)δ: 3.4(2H, br), 3.85(3H, s), 4.98(1H, d, J=4 Hz), 5.02(2H, bs), 5.5(1H, dd, J=4 & 8 Hz), 6.74(1H, s), 7.25(2H, bs), 7.47(2H, d, J=8 Hz), 7.85(2H, d, J=8 Hz), 7.99(2H, s), 9.4(1H, d, J=8 Hz)

EXAMPLE 15

Sodium 7β-[2-(2-aminothiazol-4-yl)-(Z)-2-methoxyiminoacetamido]-3-(thiazol-4-ylmethoxy)-3-cephem-4-carboxylate MP: 150°–155° C. (decomposed)
IR(KBr)cm⁻¹: 1760, 1620, 1535, 1415, 1370
NMR(DMSO-d₆)δ: 3.4(m), 3.82(3H, s), 4.95(1H, d, J=5 Hz), 5.08(2H, s), 5,45(1H, dd, J=5 & 9 Hz), 6.71(1H, s), 7.18(2H, br), 7.72(1H, s), 9.02(1H, s), 9.45(1H, d, J=9 Hz)

EXAMPLE 16

Sodium 7β-[2-(2-aminothiazol-4-yl)-(Z)-2-methoxyiminoacetamido]-3-(4-methylthiazol-2-ylmethoxy)-3-cephem-4-carboxylate MP: 175°–180° C. (decomposed)
IR(KBr)cm⁻¹: 1760, 1615, 1530, 1365

NMR(DMSO-d$_6$)δ: 2.35(3H, s), 3.4(m), 3.85(3H, s), 5.0(1H, d, J=5 Hz), 5.21(2H, s), 5.5(1H, m), 6.72(1H, s), 7.22(3H, bs), 9.5(1H, bd, J=8 Hz)

EXAMPLE 17

Sodium 7β-[2-(2-aminothiazol-4-yl)-(Z)-2-methoxyiminoacetamido]-3-(2-methylthiazol-5-ylmethoxy)-3-cephem-4-carboxylate MP: 170°–175° C. (decomposed)
IR(KBr)cm$^{-1}$: 1760, 1615, 1535, 1360
NMR(DMSO-d$_6$)δ: 2.62(3H, s), 3.4(m), 3.85(3H, s), 4.97(1H, d, J=5 Hz), 5.15(2H, s), 5.5(1H, m), 6.72(1H, s), 7.25(2H, br), 7.55(1H, s), 9.5(1H, bd, J=8 Hz)

EXAMPLE 18

Sodium 7δ-[2-(2-aminothiazol-4-yl)-(Z)-2-methoxyiminoacetamido]-3-(1,2,3-thiadiazol-4-yl)-3-cephem-4-carboxylate MP: 160°–165° C. (decomposed)
IR(KBr)cm$^{-1}$: 1760, 1620, 1535, 1370
NMR(DMSO-d$_6$)δ: 3.4(m), 3.85(3H, s), 4.98(1H, d, J=5 Hz), 5.5(3H, m), 6.72(1H, s), 7.2(2H, br), 9.35(1H, s), 9.46(1H, d, J=9 Hz)

EXAMPLE 19

Sodium 7β-[2-(2-aminothiazol-4-vl)-(Z)-2-methoxyiminoacetamido]-3-(1-methylimidazol-2-ylmethoxy)-3-cephem -4-carboxylate MP: 160°–165° C. (decomposed)
IR(KBr)cm$^{-1}$: 1760, 1660, 1610, 1535, 1360
NMR(DMSO-d$_6$)δ: 3.4(m), 3.72(3H, s), 3.86(3H, s), 4.95–5.05(3H, m), 5.5(1H, m), 6.75(1H, s), 6.82(1H, s), 7.12(1H, s), 7.22(2H, br), 9.5(1H, br)

EXMAPLE 20

Sodium 7β-[2-(2-aminothiazol-4-yl)-(Z)-2-methoxyiminoacetamido]-3-[(5S)-(2-pyrrolidon-5-ylmethoxy)]-3-cephem-4-carboxylate MP: 190°–195° C. (decomposed)
IR(KBr)cm$^{-1}$: 1760, 1670, 1530, 1365
NMR(DMSO-d$_6$)δ: 1.9–2.3(4H, m), 3.4(m), 3.6(2H, m), 3.88(3H, s), 4.1(1H, m), 5.04(1H, d, J=5 Hz), 5.5(1H, dd, J=5 & 8 Hz), 6.75(1H, s), 7.25(2H, br), 9.32(1H, br), 9.5(1H, d, J=8 Hz)

EXAMPLE 21

Sodium 7β-[2-(2-aminothiazol-4-yl)-(Z)-2-methoxyiminoacetamido]-3-[(5RS)-(2-pyrrolidon-5-ylmethoxy)]-3-cephem-4-carboxylate MP: 185°–190° C. (decomposed)
IR(KBr)cm$^{-1}$: 1760, 1670, 1530, 1365
NMR(DMSO-d$_6$)δ: 1.9–2.3(4H, m), 3.4(m), 3.5–3.7(2H, m), 3.85(3H, s), 4.0(1H, m), 5.0(1H, d, J=5 Hz), 5.45(1H, m), 6.75(1H, s) 7.2(2H, br), 8.8–9.6(2H, m)

EXAMPLE 22

Disodium 7β-[2-(2-aminothiazol-4-yl)-(Z)-2-carboxylatomethoxyiminoacetamido]-3-(4-carbamoylbenzyloxy)-3-cephem-4-carboxylate MP: 185°–190° C. (decomposed)
IR(KBr)cm$^{-1}$: 1755, 1660, 1615, 1530
NMR(DMSO-d$_6$)δ: 3.36(2H, br), 4.3(2H, br), 4.98(1H, d, J=4 Hz), 5.0(2H, s), 5.5(1H, dd, J=4 & 8 Hz), 6.8(1H, s), 7.26(2H, bs), 7.44(2H, d, J=8 Hz), 7.85(2H, d, J=8 Hz), 8.02(2H, s), 11.57(1H, d, J=8 Hz), 6.72(1H, s), 7.3(4H, m), 7.84(2H, d, J=8 Hz), 9.45(1H, bd, J=8 Hz)

EXAMPLE 23

Disodium 7β-[2-(2-aminothiazol-4-yl)-(Z)-2-carboxylatomethoxyiminoacetamido]-3-benzyloxy-3-cephem-4-carboxylate MP: 180°–185° C. (decomposed)
IR(KBr)cm$^{-1}$: 1760, 1610, 1540, 1410, 1370
NMR(DMSO-d$_6$)δ: 3.4(m), 4.28(2H, s), 4.95(3H, m), 5.5(1H, m), 6.82(1H, s), 7.38(5H, m)

EXAMPLE 24

Disodium 7β-[2-(2-aminothiazol-4-yl)-(Z)-2-carboxylatomethoxyiminoacetamido]-3-[(5RS)-(2-pyrrolidon-5-yl-methoxy)]-3-cephem-4-carboxylate MP: 155°–160° C. (decomposed)
IR(KBr)cm$^{-1}$: 1760, 1670, 1600, 1530, 1360
NMR(DMSO-d$_6$)δ: 1.9–2.2(4H, m), 3.4(m), 3.5–3.7(2H, m), 3.9–4.1(1H, m), 4.3(2H, s), 5.02(1H, d, J=5 Hz), 5.5(1H, m), 6.82(1H, s), 7.2(2H, br), 8.8–9.2(1H, m), 11.6(1H, br)

EXAMPLE 25

Disodium 7β-[2-(2-aminothiazol-4-y))-(Z)-2-carboxylatomethoxyiminoacetamido]-3-(thiazol-4-ylmethoxy)-3-cephem-4-carboxylate MP: 70°–80° C. (decomposed)
IR(KBr)cm$^{-1}$: 1760, 1610, 1535, 1415, 1380
NMR(DMSO-d$_6$)δ: 3.4(m), 4.28(2H, s), 4.96(1H, d, J=5 Hz), 5.09(2H, br), 5.5(1H, m), 6.82(1H, s), 7.18(2H, br), 7.78(1H, s), 9.06(1H, s)

EXAMPLE 26

Disodium 7β-[2-(2-aminothiazol-4-yl)-(Z)-2-carboxylatomethoxyiminoacetamido]-3-(4-methylthiazol-2-ylmethoxv)-3-cephem-4-carboxylate MP: 175°–180° C. (decomposed)
IR(KBr)cm$^{-1}$: 1760, 1610, 1530, 1410, 1370
NMR(DMSO-d$_6$)δ: 2.34(3H, s), 3.4(m), 4.3(2H, bs), 5.0(1H, d, J=5 Hz), 5.2(2H, bs), 5.5(1H, m), 6.82(1H, s), 7.2(3H, bs)

EXAMPLE 27

Disodium 7β-[2-(2-aminothiazol-4-yl)-(Z)-2-carboxylatomethoxyiminoacetamido]-3-(2-methylthiazol-5-ylmethoxy)-3-cephem-4-carboxylate MP: 170°–175° C. (decomposed)

IR(KBr)cm$^{-1}$: 1760, 1610, 1530, 1410
NMR(DMSO-d$_6$)δ: 2.62(3H, s), 3.4(m), 4.3(2H, bs), 4.98(1H, d, J=5 Hz), 5.14(2H, s), 5.5(1H, m), 6.82(1H, s), 7.25(2H, br), 7.55(1H, s)

EXAMPLE 28

Disodium
7β-[2-(2-aminothiazol-4-yl)-(Z)-2-carboxylatomethoxyiminoacetamido]-3-(1,2,3-thiadiazol-4-ylmethoxy)-3-cephem-4-carboxylate MP: 160°-165° C. (decomposed)
IR(KBr)cm$^{-1}$: 1760, 1600, 1535, 1410, 1370
NMR(DMSO-d$_6$)δ: 3.4(m), 4.28(2H, s), 4.96(1H, d, J=5 Hz), 5.45(3H, m), 6.8((1H, s), 7.18(2H, br), 9.31(1H, s)

EXAMPLE 29

Disodium
7β-[2-(2-aminothiazol-4-yl)-(Z)-2-carboxymethoxyiminoacetamido]-3-(1-methylimidazol-2-yl-methoxy)-3-cephem-4-carboxylate MP: 155°-160° C. (decomposed)
IR(KBr)cm$^{-1}$: 1760, 1620, 1535, 1410, 1370
NMR(DMSO-d$_6$)δ: 3.4(m), 3.7(3H, s), 4.28(2H, s), 4.9-5.1(3H, m), 5.4(1H, m), 6.82(2H, s), 7.12(1H, s), 7.16(2H, br)

EXAMPLE 30

Disodium
7β-[2-(2-aminothiazol-4-yl)-(Z)-2-methoxyiminoacetamido]-3-(4-carboxylatobenzyloxy)-3-cephem-4-carboxylate 1.14 g (1.5 mmol) of p-methoxybenzyl 7β-[2-(2-tritylaminothiazol-4-yl)-(Z)-2-methoxyacetamido]-3-hydroxy-3-cephem-4-carboxylate and 472 mg (1.8 mmol) of triphenylphosphine were dissolved in 20 ml of tetrahydrofuran, and a solution of 537.1 mg (1.8 mmol) of benzhydryl p-hydroxymethylbenzoate in 10 ml of tetrahydrofuran was added thereto at −20° C. under nitrogen atmosphere. Then, a tetrahydrofuran solution (10 ml) of 0.28 ml (1.8 mmol) of diethylazodicarboxylate was added thereto at the same temperature, and the mixture was stirred for 20 minutes. Ethyl acetate was added to the reaction solution. The solution was washed sequentially with water, a 1N hydrochloric acid aqueous solution, a saturated sodium hydrogencarbonate aqueous solution and a saturated sodium chloride aqueous solution and dried over magnesium sulfate. The solvent wad distilled off and the residue was purified by silica gel column chromatography (Wakogel C-300, elution with dichloromethane-chloroform) to obtain 1.28 g (yield: 80.5%) of p-methoxybenzyl 7β-[2-(2-tritylaminothiazol-4-yl)-(Z)-2-methoxyiminoacetamido]-3-(4-diphenylmethoxycarbonylbenzyloxy)-3-cephem-4-carboxylate as a powder. 1.2 g (1.13 mmol) of this powder was dissolved in 12 ml of anisole. 12 ml of trifluoroacetic acid was added thereto under cooling with ice, and the mixture was stirred for 30 minutes at the same temperature. The solvent was distilled off and isopropyl ether was added to the residue to obtain the trifluoroacetate of the above-identified compound as a powder. This powder was dissolved in water and adjusted to pH7.6 with a sodium hydrogencarbonate aqueous solution. The solution was purified by reversed phase column chromatography (Chemco LC-SORD, SP-B-ODS, elution with 10% methanol aqueous solution) and freeze-dried to obtain 312 mg (yield: 53.8%) of the above-identified compound.

MP: 190°-195° C. (decomposed)
IR(KBr)cm$^{-1}$: 1760, 1600, 1540, 1380
NMR(DMSO-d$_6$)δ: 3.4(m), 3.82(3H, s), 4.98(3H, m), 5.5(1H, m)

EXAMPLE 31

Trisodium
7β-[2-(2-aminothiazol-4-yl)-(Z)-2-carboxylatomethoxyiminoacetamido]-3-(4-carboxylatobenzyloxy)-3-cephem-4-carboxylate The above-identified compound was synthesized in the same manner as in Example 30.
MP: 160°-165° C. (decomposed)
IR(KBr)cm$^{-1}$: 1760, 1620, 1535, 1380
NMR(DMSO-d$_6$+D$_2$O)δ: 3.35(2H, m), 4.48(2H, br), 4.98(3H, m), 5.48(1H, d, J=5 Hz), 6.82(1H, s), 7.34(2H, d, J=9 Hz), 7.84(2H, d, J=9 Hz)

EXAMPLE 32

7β-[2-(2-aminothiazol-4-yl)-(Z)-2-methoxyiminoacetamido]-3-(1-methyl-4-pyridiniomethoxy)-3-cephem-4-carboxylate 492 mg (0.577 mmol) of p-methoxybenzyl 7β-[2-(2-tritylaminothiozol-4-yl)-(Z)-2-methoxyiminoacetamido]-3-(4-pyridylmethoxy)-3-cephem-4-carboxylate prepared in the same manner as in Example 1 was dissolved in 58 ml of acetone, and 2.1 ml (34 mmol) of methyl iodide was added thereto. The mixture was stirred at room temperature overnight. The solvent was distilled off and triturated with ethyl ether to obtain 541 mg (yield: 94.2%) of p-methoxybenzyl 7β-[2-(2-tritylaminothiazol-4-yl)-(Z)-2-methoxyiminoacetamido]-3-(1-methyl-4-pyridiniomethoxy)-3-cephem-4-carboxylate iodide as a yellow powder. 519 mg (0.522 mmol) of this powder was dissolved in 2.9 ml of dichloromethane and 0.92 ml of anisole, and 4.6 ml of trifluoroacetic acid was added thereto under cooling with ice. The mixture was stirred for 1 hour at the same temperature. The solvent was distilled off and isopropyl ether was added to the residue to obtain the trifluoroacetate of the above-identified compound as a powder. This powder was dissolved in water and adjusted to pH 6.5 with a sodium hydrogencarbonate aqueous solution. The solution was purified by reversed phase column chromatography (Chemco LC-SORB, SP-B-ODS, elution with 30% methanol aqueous solution), and freeze-dried to obtain 88.5 mg (yield: 33.6%) of the above-identified compound.

MP: 140° C. (decomposed)
IR(KBr)cm$^{-1}$: 1760, 1650, 1610, 1535
NMR(DMSO-d$_6$)δ: 3.84(3H, s), 4.33(3H, bs), 5.0(1H, d, J=5Hz), 5.27(2H, bs), 5.5(1H, dd, J=5 & 8Hz), 6.76(1H, s), 7.22(2H, br), 8.16(2H, d, J=4Hz), 9.93(2H, d, J=4 Hz), 9.49(1H, d, 8 Hz)

The following compounds of Examples 33–49 were synthesized in the same manner as in Example 32.

EXAMPLE 33

7β-[2-(2-aminothiazol-4-yl)-(Z)-2-ethoxyiminoacetamido]-3-[1-methyl-4-pyridiniomethoxy-3-cephem-4-carboxylate MP: 150° C. (decomposed)
IR(KBr)cm$^{-1}$: 1760, 1645, 1620, 1530

NMR(DMSO-d$_6$)δ: 1.22(3H, t, J=7 Hz), 4.09(2H, q, J=7 Hz), 4.32(3H, bs), 4.99(1H, d, J=4.5 Hz), 5.25(2H, bs), 5.51(1H, dd, J=4.5 & 8 Hz), 6.71(1H, s), 7.18(2H, br), 8.13(2H, d, J=5 Hz), 8.92(2H, d, J=5 Hz), 9.42(1H, d, J=8 Hz)

EXAMPLE 34

7β-[2-(2-aminothiazol-4-yl)-(Z)-2-benzyloxyiminoacetamido]-3-(1-methyl-4-pyridiniomethoxy)-3-cephem-4-carboxylate MP: 165° C. (decomposed)
IR(KBr)cm$^{-1}$: 1760, 1660, 1645, 1610, 1530
NMR(DMSO-d$_6$)δ: 4.3(3H, bs), 4.98(1H, d, J=4.5 Hz), 5.13(2H, bs), 5.23(2H, bs), 5.5(1H, dd, J=4.5 & 8 Hz), 6.72(1H, s), 7.2(2H, br), 7.33(5H, bs), 8.12(2H, d, J=6 Hz), 8.9(2H, d, J=6 Hz), 9.55(1H, d, J=8 Hz)

EXAMPLE 35

Sodium 7β-[2-(2-aminothiazoli4-yl)-(Z)-2-carboxylatomethoxyiminoacetamido]-3-(1-methyl-4-pyridiniomethoxy)-3-cephem-4-carboxylate MP: 130° C. (decomosed)
IR(KBr)cm$^{-1}$: 1760, 1600, 1540
NMR(DMSO-d$_6$)δ: 3.48, 3.78(2H, ABq, J=17 Hz), 4.58(3H, s), 5.23(1H, d, J=4.5 Hz), 5.3(2H, s), 5.71(1H, d, J=4.5 Hz), 7.03(1H, s), 8.03(2H, d, J=5 Hz), 8.71(2H, d, J=5 Hz)

EXAMPLE 36

Sodium 7β-[2-(2-aminothiazol-4-yl)-(Z)-2-(1-carboxylato-1-methylethoxyimino)acetamido]-3-(1-methy-4-pyridiniomethoxy)-3-cephem-4-carboxylate MP: 155° C. (decomposed)
IR(KBr)cm$^{-1}$: 1760, 1640, 1585, 1530
NMR(DMSO-d$_6$+D$_2$O)δ: 4.86(1H, bs), 5.01(3H, bss), 5.16(1H, bs), 5.53(1H, m), 6.9(1H, s), 7.26(2H, br), 7.4(2H, d, J=5 Hz), 8.49(2H, d, J=5 Hz)

EXAMPLE 37

Sodium 7β-[2-(2-aminothiazol-4-yl)-(Z)-2-(1-carboxylatovinyloxyimino)acetamido]-3-(1-methyl-4-pyridiniomethoxy)-3-cephem-4-carboxylate MP: 145° C. (decomposed)
IR(KBr)cm$^{-1}$: 1760, 1640, 1595, 1530
NMR(DMSO-d$_6$+D$_2$O)δ: 3.45(2H, bs), 4.29(3H, bs), 4.9(1H, bs), 5.01(1H, d, J=4.5 Hz), 5.16(1H, bs), 5.52(1H, d, J=4.5 Hz), 6.92(1H, s), 8.1(2H, d, J=6 Hz), 8.8(2H d, J=6 Hz)

EXAMPLE 38

Sodium 7β-[2-(2-aminothiazol-4-yl)-(Z)-2-(α-carboxylato-3,4-dihydroxybenzyloxyimino)acetamido]-3-(1-methyl-4-pyridiniomethoxy)-3-cephem-4-carboxylate (diastereisomer A)

MP: 170° C. (decomposed)
IR(KBr)cm$^{-1}$: 1760, 1570, 1530

EXAMPLE 39

Sodium 7β-[2-(2-aminothiazol-4-yl)-(Z)-2-(α-carboxylato-3,4-dihydroxvbenzVloxyimino)acetamido]-3-(1-methyl-4-pyridiniomethoxy)-3-cephem-4-carboxylate (diastereisomer B)

MP: 175° C. (decomposed)
IR(KBr)cm$^{-1}$: 1760, 1570, 1530

EXAMPLE 40

Sodium 7β-[2-(2-aminothiazol-4-yl)-(Z)-2-(2-carboxylatomethylbenzyloxyimino)acetamido]-3-(1-methyl-4-pyridiniomethoxy)-3-cephem-4-carboxylate MP: 145° C.
IR(KBr)cm$^{-1}$: 1760, 1645, 1585, 1535
NMR(DMSO-d$_6$+D$_2$O)δ: 3.34(2H, s), 4.27(3H, s), 4.98(1H, d, J=4.5 Hz), 5.23(2H, bs), 5.5(1H, d, J=4.5 Hz), 6.73(1H, s), 7.13(4H, br), 8.1(2H, bd, J=5 Hz), 8.79(2H, bd, J=5 Hz)

EXAMPLE 41

7β-[2-(5-amino-1,2,4-thiadiazol-3-yl)-(Z)-2-ethoxyiminoacetamido]-3-(1-methyl-4-pyridiniomethoxy)-3-cephem-4-carboxylate MP: 140° C. (decomposed)
IR(KBr)cm$^{-1}$: 1760, 1670, 1640, 1610, 1520
NMR(DMSO-d$_6$)δ: 1.25(3H, t, J=8 Hz), 3.53(2H, bs), 4.16(2H, m), 4.32(3H, s), 4.98(1H, d, J=5 Hz), 5.23(2H, bs), 5.55(1H, dd, J=5 & 8 Hz), 8.13(2H, d, J=5 Hz), 8.92(2H, d, J=5 Hz), 9.43(1H, d, J=9 Hz)

EXAMPLE 42

7β-(D-2-amino-2-phenylacetamido)-3-(1-methyl-4-pyridiniomethoxy)-3-cephem-4-carboxylate MP: 130° C. (decomposed)
IR(KBr)cm$^{-1}$: 1760, 1665, 1640, 1600
NMR(DMSO-d$_6$+D$_2$O)δ: 3.4(2H, bs), 4.3(3H, s), 4.4(2H, bs), 4.9(1H, m), 5.06(1H, s), 5.4(1H, s), 7.32(5H, m). 8.1(2H, m), 8.85(2H, m)

EXAMPLE 43

7β-[2-(2-aminothiazol-4-yl)-(Z)-2-methoxyiminoacetamido]-3-(1-methyl-3-pyridiniomethoxy)-3-cephem-4-carboxylate MP: 155° C. (decomposed)
IR(KBr)cm$^{-1}$: 1760, 1580–1680, 1535
NMR(DMSO-d$_6$)δ: 3.82(3H, s), 4.34(3H, s), 4.95(1H, d, J=4.5 Hz), 5.13(2H, s), 5.45(1H, dd, J=4.5 & 7.5 Hz), 6.71(1H, s), 7.17(2H, br), 7.9–8.2(1H, m), 8.57(1H, d, J=8 Hz), 8.89(1H, d, J=5 Hz), 9.32(1H, bs), 9.43(1H, d, J=7.5 Hz)

EXAMPLE 44

7β-[2-(2-aminothiazol-4-yl)-(Z)-2-methoxyiminoacetamido]-3-(1-methyl-2-pyridiniomethoxy)-3-cephem-4-carboxylate MP: 150° C. (decomposed)
IR(KBr)cm$^{-1}$: 1760, 1660, 1630, 1600
NMR(DMSO-d$_6$)δ: 3.53(2H, bs), 3.84(3H, s), 4.33(3H, bs), 4.97(1H, d, J=4.5 Hz), 5.3–5.6(3H, m), 6.74(1H, s), 7.2(2H, br), 7.85–8.15(1H, m), 8.15–8.4(1H, m), 8.4–8.7(1H, m), 8.9–9.2(1H, m), 9.47(1H, bd, J=8 Hz)

EXAMPLE 45

7β-[2-(2-aminothiazol-4-yl)-(Z)-2-(2-fluoroethox-yimino)acetamido]-3-(1-methyl-4-pyridiniomethoxy)-3-cephem-4-carboxylate MP: 148°–151° C. (decomposed)
IR(KBr)cm$^{-1}$: 1760, 1600 1680, 1530
NMR(DMSO-d$_6$)δ: 4.00–4.93(7H, m), 4.98(1H, d, J=5 Hz), 5.23(2H, bs), 5.50(1H, dd, J=5 & 8 Hz), 6.74(1H, s), 7.20(2H, br), 8.11(2H, d, J=5 Hz), 8.90(2H, d, J=5 Hz), 9.48(1H, d, J=8 Hz)

EXAMPLE 46

7β-[2-(2-aminothiazol-4-yl)-(Z)-2-methox-yiminoacetamido]-3-(1-propyl-4-pyridiniomethoxy)-3-cephem -4-carboxylate MP: 128°–130° C. (decomposed)
IR(KBr)cm$^{-1}$: 1760, 1560–1700, 1530
NMR(DMSO-d$_6$)δ: 0.85(3H, t, J=7 Hz), 1.6–2.2(2H, m), 3.83(3H, s), 4.3–4.7(2H, m), 4.9(1H, d, J=4.5 Hz), 5.26(2H, bs), 5.46(1H, dd, J=4.5 & 8 Hz), 6.72(1H, s), 7.2(2H, bs), 8.16(2H, d, J=5 Hz), 9.03(2H, d, J=5 Hz), 9.45(1H, d, J=8 Hz)

EXAMPLE 47

7β-[2-(2-aminothiazol-4-yl)-(Z)-2-methox-yiminoacetamido]-3-(1-allyl-4-pyridiniomethoxy)-3-cephem-4-carboxylate MP: 145°–150° C. (decomposed)
IR(KBr)cm$^{-1}$: 1760, 1560–1700, 1530
NMR(DMSO-d$_6$)δ: 3.85(3H, s), 5.0(1H, d, J=4.5 Hz), 5.1–5.6(7H, m), 5.9–6.4(1H, m), 6.75(1H, s), 7.18(2H, bs), 8.1–8.3(2H, m), 8.8–9.1(2H, m)

EXAMPLE 48

7β-[2-(2-aminothiazol-4-yl)-(Z)-2-methox-yiminoacetamido]-3-[1-(1-methyl-4-pyridinio)ethoxy]-3-cephem-4-carboxylate MP: 120–122° C. (decomposed)
IR(KBr)cm$^{-1}$: 1755, 1640, 1610, 1530

EXAMPLE 49

7β-[2-(2-aminothiazol-4-yl)-(Z)-2-methox-Viminoacetamido]-3-(1-carbamoylmethyl-4-pvridiniomethoxy)-3-cephem-4-carboxylate MP: 130°–135° C. (decomposed)
IR(KBr)cm$^{-1}$: 1760, 1560–1720, 1530
NMR(DMSO-d$_6$+D$_2$O)δ: 3.1–3.6(2H, m), 5.02(1H, d, J=4.5 Hz), 5.35(2H, bs), 5.53(1H, d, J=4.5 Hz), 6.78(1H, s), 8.19(2H, d, J=5 Hz), 8.83(2H, d, J=5 Hz)

EXAMPLE 50

Sodium 7β-[2-(2-aminothiazol-4-yl)-(Z)-2-methox-yiminoacetamido]-3-(1-carboxylatomethyl-4-pyridiniomethoxy) -3-cephem-4-carboxylate 800 mg (0.938 mmol) of p-methoxybenzyl 7β-[2-(2-tritylaminothiazol-4-yl)-(Z)-2-methox-yiminoacetamido]-3-(4-pyridylmethoxy)-3-cephem-4-carboxylate obtained in the same manner as in Example 1 was dissolved in 93 ml of acetone, and 3.34 g (9.49 mmol) of benzhydryl iodoacetate and a few drops of N,N-dimethylformamide were added thereto. The mixture was stirred overnight at room temperature. The solvent was distilled off, and the residue was triturated with ethyl ether to obtain 1.33 g of a powder. 1.3 g of this powder was dissolved in 6 ml of dichloromethane and 1.3 ml of anisole, and 9 ml of trifluoroacetic acid was added thereto under cooling with ice. The mixture was stirred for 1 hour at the same temperature. The solvent was distilled off and isopropyl ether was added to the residue to obtain the trifluoroacetate of the above-identified compound. The trifluoroacetate was dissolved in water and adjusted to pH7.0 with a sodium hydrogencarbonate aqueous solution. Then, the solution was purified by reversed phase column chromatography (Chemco LC-SORB, SP-B-ODS, elution with 30% methanol aqueous solution), and freeze-dried to obtain 133 mg (yield: 21.8%) of the above-identified compound.

MP: 150° C. (decomposed)
IR(KBr)cm$^{-1}$: 1760, 1640, 1535
NMR(DMSO-d$_6$)δ: 3.83(3H, s), 4.93(2H, bs), 5.03(1H, d, J=4.5 Hz), 5.27(2H, bs), 5.52(1H, dd, J=4.5 & 8 Hz), 6.74(1H, s), 7.22(2H, bs), 8.07(2H, d, J=6 Hz), 8.78(2H, d, J=6 Hz), 9.53(1H, d, J=8 Hz)

The following compounds of Examples 51 and 52 were synthesized in the same manner as in Example 50.

EXAMPLE 51

Sodium 7β-[2-(2-aminothiazol-4-yl)-(Z)-2-ethox-yiminoacetamido]-3-(1-carboxylatomethyl-4-pyridiniomethoxy)-3-cephem-4-carboxylate MP: 150° C. (decomposed)
IR(KBr)cm$^{-1}$: 1760, 1640, 1530
NMR(DMSO-d$_6$)δ: 1.22(3H, t, J=7 Hz), 4.08(2H, q, J=7 Hz), 4.9(2H, bs), 5.01(1H, d, J=4.5 Hz), 5.25(2H, bs), 5.52(1H, dd, J=4.5 & 7 Hz), 6.71(1H, s), 7.2(2H, bs), 8.05(2H, d, J=5 Hz), 8.76(2H, d, J=5 Hz), 20. 9.46(1H, d, J=7 Hz)

EXAMPLE 52

Disodium 7β-[2-(2-aminothiazol-4-yl)-(Z)-2-carboxylatomethox-yiminoacetamido]-3-(1-carboxylatomethyl-4-pyridiniomethoxy)-3-cephem-4-carboxylate MP: 150° C. (decomposed)
IR(KBr)cm$^{-1}$: 1760, 1580–1700, 1540
NMR(DMSO-d$_6$)δ: 3.5, 3.8(2H, ABq, J=18 Hz), 4.59(2H, s), 5.18(1H, d, J=4 Hz), 5.21(2H, s), 5.35(2H, s), 5.73(1H, d, J=4 Hz), 7.06(1H, s), 8.07(2H, d, J=6 Hz), 8.7(2H, d, J=6 Hz)

EXAMPLE 53

7β-[2-(2-aminothiazol-4-yl)-(Z)-2-methox-yiminoacetamido]-3-(3,4-dihydroxy-1-methyl-6-pyridiniomethoxy)-3-cephem-4-carboxylate 340 mg (0.446 mmol) of p-methoxybenzyl 7β-[2-(2-tritylaminothiazol-4-yl)-(Z)-2-methox-yiminoacetamido]-3-hydroxy-3-cephem-4-carboxylate and 146 mg (0.557 mmol) of triphenylphosphine were dissolved in 7 ml of tetrahydrofuran, and a solution of tetrahydrofuran (3.5 ml) of 170 mg (0.446 mmol) of 4,5-bis(4-methoxybenzyloxy)-2-hydroxymethylpyridine was added thereto at −20° C. under nitrogen atmosphere. Then, a solution of 0.087 ml (0.55 mmol) of diethylazodicarboxylate in 3.5 ml of tetrahydrofuran was dropwise added to the solution at -20° C., and the mixture was stirred for 1 hour at the same temperature. 30 ml of ethylacetate was added thereto. The solution was washed sequentially with water, a 1N hydrochloric acid aqueous solution, a saturated sodium hydrogencarbonate aqueous solution and a saturated sodium chloride aqueous solution and dried over magnesium sulfate. The solvent was distilled off, and the residue was purified by silica gel column chromatography (Wakogel C-300, elution with 1-2% methanol-chloroform) to obtain 325 mg (yield: 64.8%) of p-methoxybenzyl 7β-[2-(2-tritylaminothiazol-4-yl)-(Z)-2-methoxyiminoacetamido]-[3,4-bis(4-methoxybenzyloxy)-6-pyridylmethoxy]-3-cephem-4-carboxylate as a powder. 325 mg (0.289 mmol) of this powder was dissolved in 28 ml of methylene chloride, and a solution of 0.067 ml (0.592 mmol) of methyltrilrate in 2 ml of methylene chloride was dropwise added thereto at −20° C. under nitrogen atmosphere. The mixture was stirred for 1 hour at room temperature. The solvent was distilled off, and the residue was triturated to obtain 355 mg (yield: 95.2%) of p-methoxybenzyl 7β-[2-(2-tritylaminothiazol-4-yl) -(Z)-2-methoxyiminoacetamido]-[3,4-bis(4-methoxybenzyloxy) -1-methyl-6-pyridiniomethoxy]-3-cephem-4-carboxylate trifluoromethanesulfonate as a powder. 355 mg (0.275 mmol) of this powder was dissolved in 429 mg (2.79 mmol) of 3-methyl-4-methylthiophenol, 2 ml of methylene chloride and 0.34 ml (2.5 mmol) of thioanisole, and 2 ml of trifluoroacetic acid was added thereto under cooling with ice. The mixture was stirred for 1 hour at room temperature. The solvent was distilled off, and ethyl ether was added to the residue to obtain the trifluoroacetate of the above-identified compound as a powder. This powder was dissolved in water and insolubles were filtered off. The filtrate was purified by reversed phase column chromatography (Chemco LC-SORB, SP-B-ODS, elution with 30% methanol aqueous solution) and freeze-dried to obtain 28.1 mg (yield: 19%) of the above-identified compound.

MP: 150°-160° C. (decomposed)

IR(KBr)cm⁻¹: 3350, 1760, 1670, 1630, 1560, 1535

NMR(DMSO-d₆)67: 3.68(3H, s), 3.86(3H, s), 5.07(2H, s), 5.18(1H, d, J=5 Hz), 5.61(1H, dd, J=5 & 8 Hz), 6.40(1H, s), 6.84(1H, s), 7.26(2H, br), 7.50(1H, s), 9.60(1H, d, J=8 Hz)

EXAMPLE 54

Sodium 7β-[2-(2-aminothiazol-4-y1)-(Z)-2-(1-carboxylato-1-methylethoxyimino)acetamido]-3-(3,4-dihydroxy -1-methyl-6-pyridiniomethoxy)-3-cephem-4-carboxylate The above-identified compound was synthesized in the same manner as in Example 53.

MP: 170-180 ° C. (decomposed)

IR(KBr)cm⁻¹: 3450, 1765, 1670, 1635, 1560

NMR(DMSO-d₆)δ: 1.44(3H, s), 1.46(3H, s), 3.68(3H, s), 5.07(2H, s), 5.20(1H, d, J=4 Hz), 5.68(1H, dd, J=4 & 8 Hz), 6.41(1H, s), 6.80(1H, s), 7.33(2H, br), 7.51(1H, s), 9.45(1H, d, J=8 Hz)

EXAMPLE 55

Pivaloyloxymethyl 7β-[2-(2-aminothiazol-4-yl)-(Z)-2-methoxyiminoacetamido]-3-(4-cyanobenzyloxy)-3-cephem-4-carboxylate 57.4 mg (0.38 mmol) of chloromethyl pivalate was dissolved in 2 ml of acetone, and 63 mg (0.42 mmol) of sodium iodide was added thereto. The mixture was heated for 30 minutes at 50° C., and 4 ml of ethyl ether was added thereto. Insolubles were filtered off and the solvent was distilled off. Then, the residue was dissolved in 1 ml of N,N-dimethylformamide. 100 mg (0.217 mmol) of sodium 7β-[2-(2-aminothiazol-4-yl)-(Z)-2-methoxyiminoacetamido]-3-(4-cyanobenzyloxy)-3-cephem-4-carboxylate prepared in the same manner as in Example 12 was dissolved in 1 ml of N,N-dimethylformamide. The above solution was added to this solution under cooling with ice and stirred for 30 minutes at room temperature. Water and ethyl acetate was added to the reaction solution, and the ethyl acetate layer was separated and washed sequentially with a saturated sodium hydrogencarbonate aqueous solution and a saturated sodium chloride aqueous solution and dried over magnesium sulfate. The solvent was distilled off and the residue was triturated with ethyl ether to obtain 24.8 mg (yield: 21.2%) of the above-identified compound.

MP: 120°-123° C. (decomposed)

IR(KBr)cm⁻¹: 1780, 1750, 1675, 1620, 1530

NMR(DMSO-d₆)δ: 1.16(9H, s), 3.78(2H, s), 3.86(3H, s), 5.11(2H, s), 5.23(1H, d, J=4 Hz), 5.73(1H, dd, J=4 & 8 Hz), 5.79, 5.89(2H, ABq, J=6 Hz), 6.81(1H, s), 7.24(2H, br), 9.64(1H, d, J=8 Hz)

The following compounds of Examples 56-57 were synthesized in the same manner as in Example 55.

EXAMPLE 56

Pivaloyloxymethyl 7β-[2-(2aminothiazol-4-yl) -(Z)-2-methoxyiminoacetamido]-3-(4-nitrobenzyloxy)-3-cephem-4-carboxylate MP: 122°-125° C. (decomposed)

IR(KBr)cm⁻¹: 1780, 1750, 1680, 1615, 1520

NMR(DMSO-d₆)δ: 1.11(9H, s), 3.64-3.94(5H, m), 5.23(1H, d, J=4 Hz), 5.40(2H, s), 5.63(1H, dd, J=4 & 8 Hz), 5.81, 5.89(2H, ABq, J=6HZ), 6.85(1H, s), 7.28(2H, br), 7.72(2H, d, J=8 Hz), 8.29(2H, d, J=8 Hz), 9.58(1H, d,J=8 Hz)

EXAMPLE 57

Pivaloyloxymethyl 7β-[2-(2-aminothiazol-4-yl)-(Z)-2-methoxyiminoacetamido]-3-(1,2,3-thiadiazol-4-yl-methoxy)-3-cephem-4-carboxylate MP: 115°-120° C. (decomposed)

IR(KBr)cm⁻¹: 1780, 1750, 1675, 1615, 1535

NMR(DMSO-d₆)δ: 1.10(9H, s), 3.8-4.0(5H, m), 5.22(1H, d, J=4 Hz), 5.6-5.9(5H, m), 6.85(1H, s), 7.3(1H, br), 9.24(1H, s),9.62(1H, d, J=8 Hz)

The compounds of the present invention have excellent antibacterial activities and are useful for treatment to bacterial infectiousness of mammal including human.

We claim:

1. A cephalosporin derivative having the formula:

$$\text{(I)}$$

wherein R¹ is a substituted amino group selected from the group consisting of:
(i) R⁴—C(=N~OR⁵)—CONH— group, wherein R⁴ is a phenyl, naphthyl, furanyl, thienyl, thiazolyl, 1,2,4-thiadiazolyl, pyridyl, isothiazolyl, oxazolyl, pyrimidyl group which may be substituted; R⁵ is a hydrogen atom or a C₁₋₆ alkyl, C₃₋₆ cycloalkyl, $C_{2-6}$ alkenyl, $C_{2-6}$ alkynyl, phenyl, naphthyl, benzyl, phenethyl, naphthylmethyl, pyridyl, furanyl, thienyl, imidazolyl, thiazolyl, isothiazolyl, isoquinolyl, quinolyl, oxazolyl, isoxazolyl, tetrazolyl group which may be substituted;

(ii) $R^4$—C(=C($R^6$))—$R^7$)—CONH— group, wherein $R^4$ is a phenyl, naphthyl, furanyl, thienyl, thiazolyl, 1,2,4-thiadiazolyl, pyridyl, isothiazolyl, oxazolyl, pyrimidyl group which may be substituted; each of $R^6$ and $R^7$, which may be the same or different, is a hydrogen atom, a halogen atom or a $C_{1-6}$ alkyl, phenyl, naphthyl, benzyl, phenethyl, naphthylmethyl group which may be substituted;

(iii) $R^8$—($Z^1$)$_n$—CH(—$R^9$)—CONH— group, wherein $R^8$ is a $C_{1-6}$ alkyl, $C_{2-6}$ alkenyl, phenyl, naphthyl, furanyl, thienyl, benzothienyl, pyridyl, tetrazolyl, oxazolyl group which may be substituted and $R^9$ is a hydrogen atom, carboxyl group, an amino group, a sulfo group, a sulfamoyl group, a carbamoyl group, a hydroxyl group, a formyloxy group, a carbamoyloxy group, $Z^1$ is an oxygen atom or a sulfur atom and n is 0 or 1;

(iv) $R^{10}$—CONH— group, wherein $R^{10}$ is a pyridyl, imidazolyl, piperazinyl, thiazolyl or oxazolyl group which may be substituted;

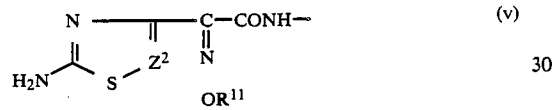

(v)

wherein $Z^2$ is a carbon atom or a nitrogen atom and $R^{11}$ is a hydrogen atom, a $C_{1-6}$ alkyl, $C_{3-6}$ cycloalkyl, $C_{2-6}$ alkenyl, $C_{2-6}$ alkynyl, phenyl, naphthyl, benzyl, phenethyl, naphthylmethyl, pyridyl, furanyl, thienyl, imidazolyl, thiazolyl, isothiazolyl, isoquinolyl, quinolyl, oxazolyl, isoxazolyl, tetrazolyl, group which may be substituted; and

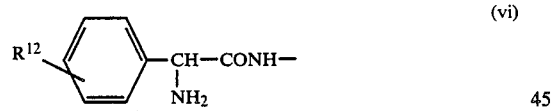

(vi)

wherein $R^{12}$ represents one or two substituents selected from the group consisting of a hydrogen atom, a hydroxyl group, an acetoxy group and a halogen atom;

X is an alkenylene group $R^2$ is a 1,2,3-thiadiazolyl. 1.2.4-thiadiazolyl, 1,3,4-thiadiazolyl, tetrazolyl, thiazolyl, isothiazolyl, pyridyl, or benzothiazolyl, which may be substituted by one or more substituents selected from the group consisting of a halogen atom, a methyl group, an ethyl group, a propyl group, a hydroxymethyl group, an aminomethyl group, a sulfomethyl group, a carboxymethyl group, a cyanomethyl group, a fluoromethyl group, a chloromethyl group, a difluoromethyl group, a trifluoromethyl group, a carbamoylmethyl group, an N-methylcarbamoylmethyl group, a sulfamoylmethyl group, an oxo group, an N-methylaminomethyl group, an amino group, a methylamino group, a dimethylamino group, an ethylamino group, a methoxy group, an ethoxy group, a fluoromethyl group, a difluoroethoxy group, a trifluoroethyl group, a sulfamoyl group, a carboxyl group, a methoxycarbonyl group, a cyano group, a nitro group, a vinyl group, an allyl group, a propargyl group, an ethynyl group, an acetoxy group, a formyloxy group, a carbamoyloxy group, an N-methylcarbamoyloxy group, an acetamide group, a formamide group, an acetyl group, a fluoroacetyl group, a difluoroacetyl group, a trifluoroacetyl group, a hydroxyl group, a cyclopropyl group, a cyclobutyl group, a cyclopentyl group and a cyclohexyl group and $R^3$ is a hydrogen atom, a negative charge or a residue of an ester which can form a pharmaceutically acceptable ester hydrolyzable in a living body; or a pharmaceutically acceptable salt thereof.

2. The derivative according to claim 1, wherein $R^2$ is a 1,2,3-thiadiazolyl, 1,2,4-thiadiazolyl, 1,3,4-thiadiazolyl, thiadiazolyl, tetradiazolyl, thiazolyl, or pyridyl.

3. The derivative according to claim 1 wherein the substituent attached to $R^2$ is a halogen atom, a methyl group, an ethel group, a propyl group, a sulfomethyl group, a carboxymethyl group, a carbamoylmethyl group, a sulfamoylmethyl group, an oxo group, an amino group, a sulfamoyl group, a carboxyl group, an allyl group, a carbamoyloxy group or a hydroxyl group.

4. An antibacterial agent comprising an antibacterially effective amount of the compound of claim 1 and a pharmaceutically acceptable carrier.

* * * * *